United States Patent
Hsieh et al.

(10) Patent No.: US 6,996,206 B2
(45) Date of Patent: Feb. 7, 2006

(54) METHOD, SYSTEM AND STORAGE MEDIUM FOR REFERENCE NORMALIZATION FOR BLOCKED REFERENCE CHANNELS

(75) Inventors: Jiang Hsieh, Brookfield, WI (US); Jean-Baptiste Thibault, Milwaukee, WI (US); Fang Frank Dong, Waukesha, WI (US); Jian ying Li, New Berlin, WI (US); Edward Chao, Oconomowoc, WI (US); Scott Matt McOlash, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/709,080

(22) Filed: Apr. 12, 2004

(65) Prior Publication Data

US 2005/0226366 A1    Oct. 13, 2005

(51) Int. Cl.
*A61B 6/03*    (2006.01)
(52) U.S. Cl. ............................ 378/19; 378/4
(58) Field of Classification Search .................. 378/4, 378/8, 19, 901; 382/131, 132, 4, 19, 207
See application file for complete search history.

(56) References Cited

U.S. PATENT DOCUMENTS

| | | | |
|---|---|---|---|
| 4,580,219 A | 4/1986 | Pelc et al. | 364/414 |
| 4,809,314 A * | 2/1989 | Steele et al. | 378/205 |
| 5,430,785 A * | 7/1995 | Pfoh et al. | 378/19 |
| 5,761,257 A * | 6/1998 | Toth et al. | 378/19 |
| 6,529,575 B1 | 3/2003 | Hsieh | 378/4 |

* cited by examiner

*Primary Examiner*—David V. Bruce
*Assistant Examiner*—Chih-Cheng Glen Kao
(74) *Attorney, Agent, or Firm*—Cantor Colburn LLP

(57) ABSTRACT

A method for performing reference normalization for an image created by an imaging system. The imaging system includes a radiation detector array with a right and left edge. The method includes receiving a projection dataset created by the imaging system in response to a varying x-ray tube current. The projection dataset includes a view and predicted fluxes are calculated for the set of reference channels within the view. A right set of reference channels are located proximate at the right edge of the detector array and a left set of reference channels are located proximate to the left edge of the detector array. The method also includes calculating average actual fluxes for the sets of reference channels. Based on the predicted reference fluxes and the average fluxes, a reference correction value for the view is determined. The correction value is applied for the reference correction of the view.

24 Claims, 2 Drawing Sheets

METHOD, SYSTEM AND STORAGE MEDIUM FOR REFERENCE NORMALIZATION FOR BLOCKED REFERENCE CHANNELS

BACKGROUND OF THE INVENTION

This invention relates generally to a method and system for reference normalization in an x-ray image, and more particularly, to a method and system for reference normalization for blocked reference channels in an x-ray image generated by a computed tomography (CT) system.

In CT imaging systems, an x-ray source projects a fan-shaped beam that is collimated to lie within an X-Y plane, generally referred to as an "imaging plane", of a Cartesian coordinate system toward an array of radiation detectors, wherein each radiation detector includes a detector element disposed within the CT system so as to receive this fan-shaped beam. An object, such as a patient, is disposed between the x-ray source and the radiation detector array so as to lie within the imaging plane and so as to be subjected to the x-ray beam, which passes through the object. As the x-ray beam passes through the object, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam intensity at the detector element location. These electrical signals are referred to as x-ray attenuation measurements or x-ray images.

Moreover, the x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object. In CT systems that employ a single detector array, the slice thickness is controlled and determined by the width of the collimator, while in CT systems that employ a multiple detector array, the slice thickness is controlled and determined by summing the contributions of a plurality of detector sub-units and by physically moving the collimator to the outer edges of each slice.

Reference normalization is an important step in CT pre-processing operations to reduce or remove the impact of the x-ray tube output fluctuation. For this purpose, a set of reference channels (also referred to herein as reference detectors) are placed slightly outside the reconstruction field of view (FOV) in the array of radiation detectors so that the reference channels receive x-ray photons directly from the x-ray source without interference from the scanned object. These reference channels monitor the x-ray tube flux and the measured signal is applied to the measured projections. The impact of any variations in the x-ray tube output on the measured projections is thereby properly removed. In a typical configuration, three reference channels are placed at the left-hand side of the array. However, for larger than normal-sized patients and/or with the scanned object off-centered, there is a greater chance that these reference channels are blocked during the scan. In addition, with the introduction of wide-bore scanners that cover a larger FOV with the same detector, the reference channels are routinely blocked by the patients. To ensure the proper functioning of the reference normalization, different correction steps have to be developed to account for situations where the reference channels are blocked.

BRIEF DESCRIPTION OF THE INVENTION

One aspect of the invention is a method for performing reference normalization for a projection created by an imaging system. The imaging system includes a radiation detector array with a right and left edge. The method includes receiving a projection dataset created by the imaging system in response to a varying x-ray tube current. The projection dataset includes a view and predicted fluxes are calculated for the set of reference channels within the view. A right set of reference channels are located proximate at the right edge of the detector array and a left set of reference channels are located proximate to the left edge of the detector array. The method also includes calculating average actual fluxes for the sets of reference channels. Based on the predicted reference fluxes and the average fluxes, a reference correction value for the view is determined. The correction value is applied for the reference correction of the view.

Another aspect of the invention is a method for performing reference normalization for a projection created by an imaging system that includes a radiation detector array with a right and left edge. The method includes operating the imaging system so as to create a projection dataset responsive to an object. The imaging system is operated at varying x-ray tube currents to create the projection dataset. The projection dataset includes a view. Predicted fluxes for the sets of reference channels within the view are calculated, wherein a right set of reference channels is located proximate at the right edge of the detector array and a left set of reference channels is located proximate to the left edge of the detector array. Average actual fluxes are calculated for the sets of reference channels. A reference correction value is determined for the view based on the predicted reference fluxes and the average actual fluxes. The reference correction value is applied to the view.

A further aspect of the invention is a medium encoded with a machine-readable computer program code for performing reference normalization for a projection created by an imaging system that includes a radiation detector array with a right and left edge. The medium includes instructions to implement a method including receiving a projection dataset created by the imaging system in response to a varying x-ray tube current, where the projection dataset includes a view. The predicted fluxes for the sets of reference channels within the view are calculated. A right set of reference channels is located proximate at the right edge of the detector array and a left set of reference channels is located proximate to the left edge of the detector array. The average actual fluxes are calculated for the sets of reference channels. The referenced corrected values are then determined based on the predicted reference fluxes and the average actual fluxes. The reference correction value is applied to the view.

Another aspect of the invention is a system for performing reference normalization for an image. The system includes a gantry having an x-ray source and a radiation detector array, wherein the gantry defines an object cavity. The x-ray source and the radiation detector array are rotatingly associated with the gantry so as to be separated by the object cavity. The detector array includes a right and left edge. An object support structure movingly associated with the gantry allows communication with the object cavity. The system also includes a processing device including instructions to implement a method that includes receiving a projection dataset created by the imaging system in response to a varying x-ray tube current. The projection dataset includes a view. Predicted fluxes for the sets of reference channels are calculated within the view, where a right set of reference channels is located proximate at the right edge of the detector array and a left set of reference channels is located proximate at the left edge of the detector array. Average actual fluxes for the sets of reference channels are calculated. A reference correction value for the view is determined based on the predicted reference fluxes and the average actual fluxes. The reference correction value is applied to the view.

Another aspect of the invention is a system for performing reference normalization for a projection. The system includes an imaging system. The imaging system includes a radiation detector array with a right and left edge. The imaging system also includes an object disposed so as to be communicated with the imaging system. The imaging system generates a projection dataset responsive to the object and to a varying x-ray tube current, where the projection dataset includes a view. The processing device receives the projection created by the imaging system. The processing device calculates predicted fluxes for the sets of reference channels within the view, where a right set of reference channels is located proximate at the right edge of the detector array and a left set of reference channels is located proximate at the left edge of the detector array. The processing device also calculates average actual fluxes for the sets of reference channels. A reference correction value is determined for the view based on the predicted reference fluxes and the average actual fluxes. The reference correction value is applied to the view.

BRIEF DESCRIPTION OF THE DRAWINGS

Referring to the exemplary drawings wherein like elements are numbered alike in the several FIGs..

DETAILED DESCRIPTION OF THE INVENTION

An exemplary embodiment of the present invention includes identifying a condition where the reference channel is blocked. When this condition occurs, the measured reference channel, or reference detector, readings should not be used for the normalization process since they no longer represent the x-ray output flux. Some of the newer imaging systems, such as models of the wide-bore scanners include features where the x-ray tube current (and therefore the output flux) changes constantly so that the average projection noise can be held roughly constant when scanning objects that vary significantly. For example, when a scan is performed from the top of the head to the bottom of the feet of a patient, the x-ray tube current will vary as a function of where the current view is located within the anatomy (e.g., neck, stomach). In another example, the x-ray tube current will vary based on the angle of the patient relative to the x-ray source (e.g., side to side, front to back). Therefore, an independent signal that is closely related to the output x-ray flux and, at the same time, is not influenced by the patient blockage must be obtained. In an exemplary embodiment of the present invention, the sampled x-ray tube current is utilized as the independent signal. During CT scanning, the input current to the x-ray tube is sampled for every view and is stored in the scan file, or projection dataset. The projection dataset includes data corresponding to one or more views associated with a scan. The conversion factor that maps the tube current to the output flux is also stored in the file, since this factor is fixed for a known scanning protocol (kV, slice thickness, etc.). Note that this factor varies between reference channels and CT systems because different detectors have different gains to the x-ray input.

Figure 1:
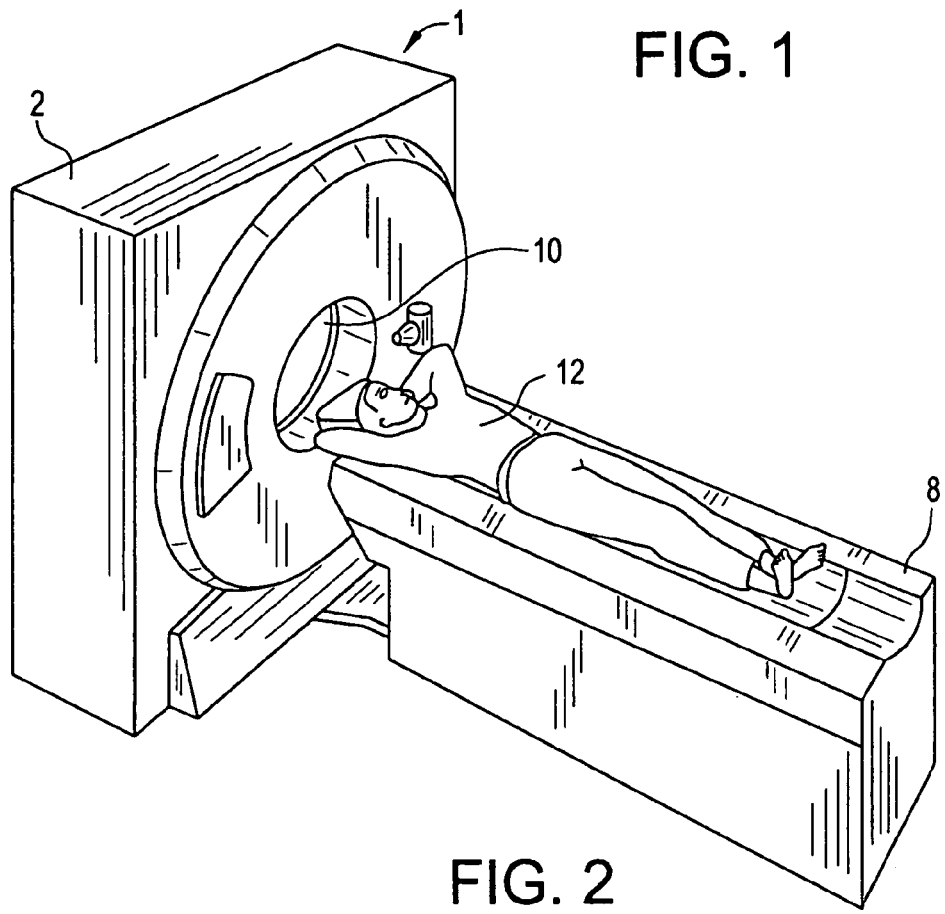
FIG. 1 is a perspective view of a CT imaging system and a patient disposed for imaging, in accordance with an exemplary embodiment of the present invention.
Figure 2:
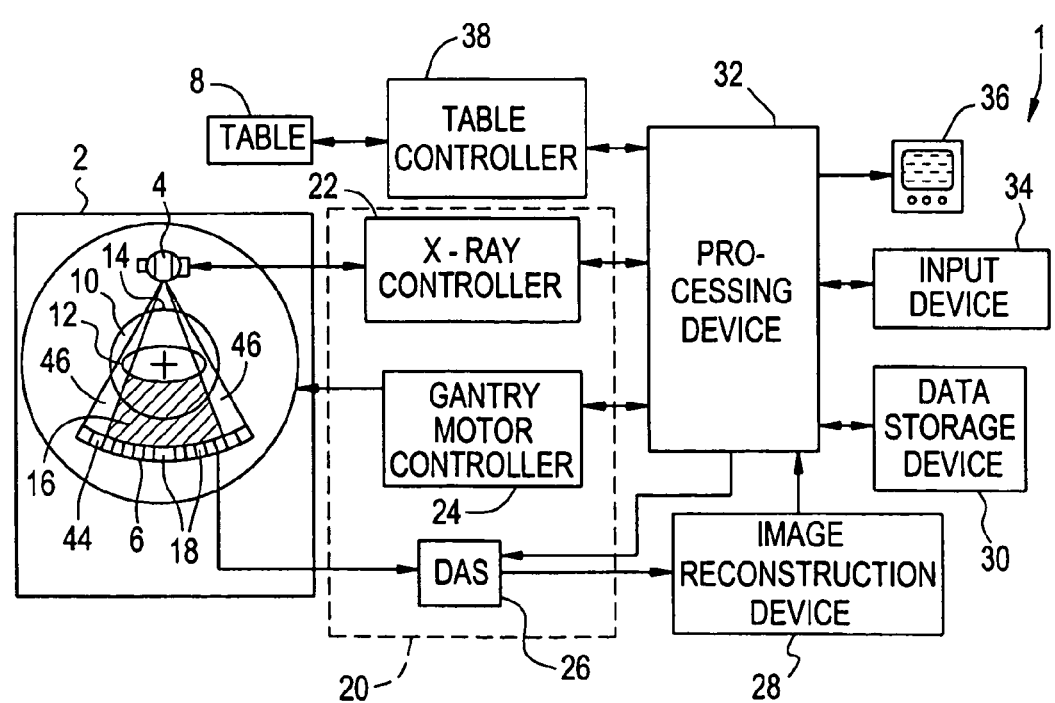
FIG. 2 is a block schematic diagram of a CT imaging system, in accordance with an exemplary embodiment of the present invention.

Referring to FIG. 1 and FIG. 2 a representative CT imaging system 1 is shown and includes a gantry 2 having an x-ray source 4, a radiation detector array 6, a patient support structure 8 and an object cavity 10. The x-ray source 4 and the radiation detector array 6 are opposingly disposed so as to be separated by the object cavity 10. An object, such as a patient 12, is disposed upon the patient support structure 8 which is then disposed within the object cavity 10. The x-ray source 4 projects an x-ray beam 14 toward the radiation detector array 6 so as to pass through the patient 12. The x-ray beam 14 is then collimated by a collimator so as to lie within an X-Y plane of a Cartesian coordinate system referred to as an "imaging plane". After passing through and becoming attenuated by the patient 12, the attenuated x-ray beam 16 is received by the radiation detector array 6. The radiation detector array 6 includes a plurality of detector elements 18. Each of the detector elements 18 receives the attenuated x-ray beam 16 and produces an electrical signal responsive to the intensity of the attenuated x-ray beam 16. In addition, some portions of the x-ray beam 16 may result in periphery sections of beams that don't pass through and become attenuated by the patient 12. These periphery sections 46 may be received by reference channels, or reference detectors 44, that are included in the radiation detector array 6 as depicted in FIG. 2 or by detector elements 18 that are at the outer edge of the radiation detector array 6.

In addition, the x-ray source 4 and the radiation detector array 6 are rotatingly disposed relative to the gantry 2 and to the patient support structure 8, so as to allow the x-ray source 4 and the radiation detector array 6 to rotate around the patient support structure 8 when the patient support structure 8 is disposed within the object cavity 10. The x-ray projection data is obtained by rotating the x-ray source 4 and the radiation detector array 6 around the patient 12 during a scan. The x-ray source 4 and the radiation detector array 6 are in communication with a control mechanism 20 associated with the CT imaging system 1. Control mechanism 20 controls the rotation and operation of x-ray source 4 and radiation detector array 6.

The control mechanism 20 includes an x-ray controller 22 that is in communication with the x-ray source 4, a gantry motor controller 24, and a data acquisition system (DAS) 26 in communication with the radiation detector array 6. The x-ray controller 22 provides power and timing signals to the x-ray source 4 and the gantry motor controller 24 controls the rotational speed and angular position of the x-ray source 4 and the radiation detector array 6. The DAS 26 receives the electrical signal data produced by the detector elements 18 and converts this data into digital signals for subsequent processing. The CT imaging system 1 also includes an image reconstruction device 28, a data storage device 30 and a processing device 32. The processing device 32 is in communication with the image reconstruction device 28, the gantry motor controller 24, the x-ray controller 22, the data storage device 30, an input device 34 and an output device 36. Moreover, the CT imaging system 1 also includes a table controller 38 in communication with the processing device 32 and the patient support structure 8, so as to control the position of the patient support structure 8 relative to the object cavity 10.

The patient 12 is disposed on the patient support structure 8, which is then positioned by an operator via the processing device 32 so as to be disposed within the object cavity 10. The gantry motor controller 24 is operated via the processing device 32 so as to cause the x-ray source 4 and the radiation detector array 6 to rotate relative to the patient 12. The x-ray controller 22 is operated via the processing device 32 so as to cause the x-ray source 4 to emit and project a collimated x-ray beam 14 toward the radiation detector array 6 and hence toward the patient 12. The x-ray beam 14 passes through the patient 12 so as to create an attenuated x-ray beam 16, which is received by the radiation detector array 6.

The detector elements 18 receive the attenuated x-ray beam 16, produce electrical signal data responsive to the intensity of the attenuated x-ray beam 16 and communicate this electrical signal data to the DAS 26. The DAS 26 then converts this electrical signal data to digital signals and communicates both the digital signals and the electrical signal data to the image reconstruction device 28, which performs high-speed image reconstruction. This information is then communicated to the processing device 32, which stores the image in the data storage device 30 and displays the digital signal as an image via the output device 36.

Figure 3:
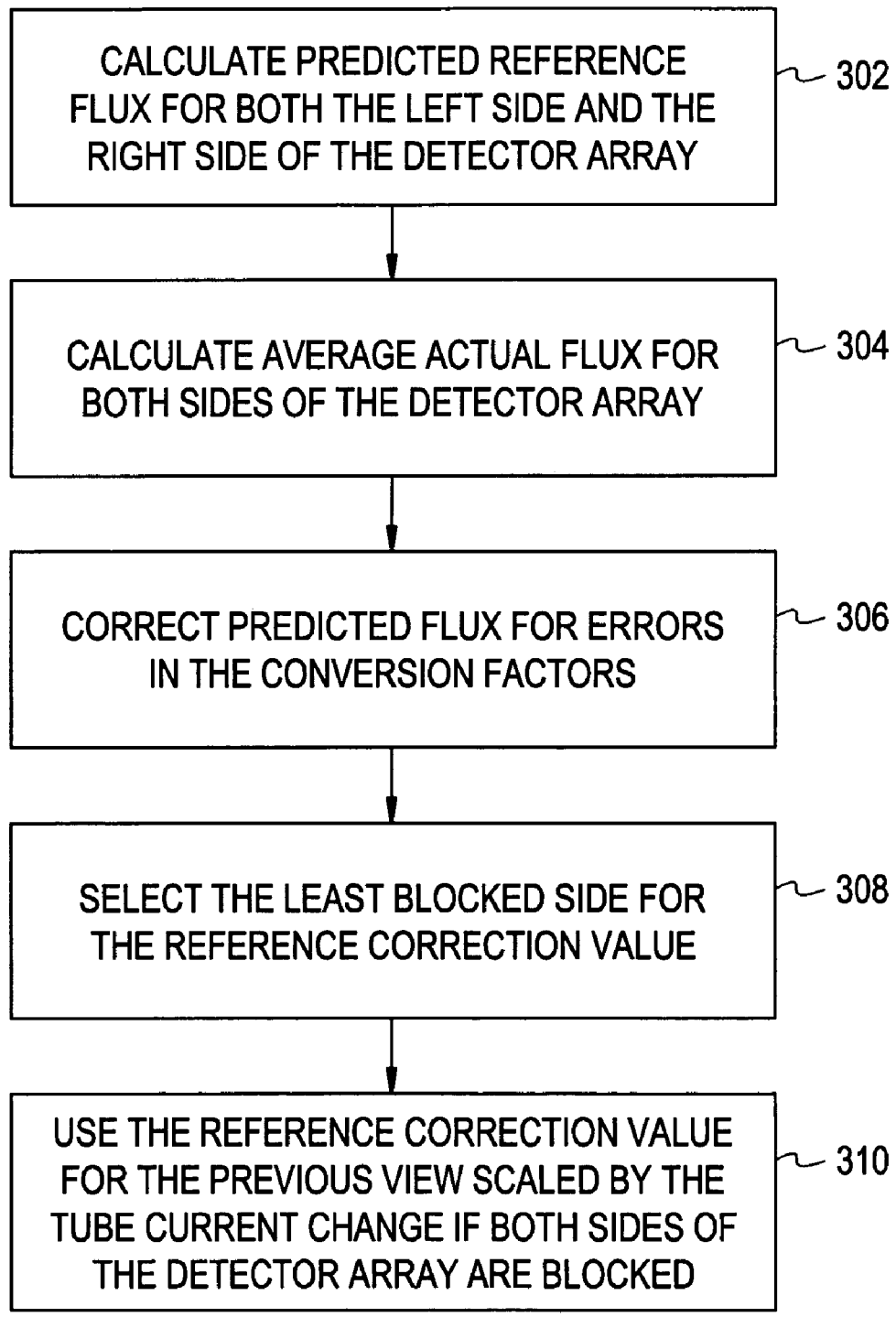
FIG. 3 is a flow diagram of a method for reference normalization for blocked reference channels in a CT imaging system in accordance with an exemplary embodiment of the present invention.

FIG. 3 is a flow diagram of a method for reference normalization for blocked reference channels in a CT imaging system in accordance with an exemplary embodiment of the present invention. The process depicted in FIG. 3 is initiated for each view within a projection dataset. At step 302, a predicted reference flux is calculated for the radiation detectors located at the leftmost side of the radiation detector array 6 (e.g., the reference channels), as well as the radiation detectors located at the rightmost side of the radiation detector array 6. The predicted x-ray flux observed at the reference channels, $f_l(t)$, may be derived as follows:

$$f_l(t) = q \cdot c(t);$$

where c(t) is the measured x-ray tube current curve, q is the conversion factor and t is the view sampling index. Because the averaged reference readings are utilized for normalization, the detector channel index is dropped. The subscript "l" in the above equation denotes the fact that most CT scanners include reference channels on the left hand side of the detector.

The predicted flux, $f_r(t)$, is also calculated for the rightmost channels. In an exemplary embodiment of the present invention, the three rightmost channels in the detector array are utilized as reference channels. It should be noted that $f_r(t)$ and $f_l(t)$ are related by a simple scaling that reflects different detector gains. This scaling factor may be determined by the ratio of the left and right channel readings during air calibration. Experiments have shown that the relationship between the recorded tube input value and the measured reference value is not linear. That is, the value of q changes with the change of x-ray tube current. Therefore, q(c) is a tube input dependent function. The function can be determined experimentally or theoretically. For example, experiments have shown that the following function holds for a wide range of x-ray tube current:

$$q(c) = q_0[1 - s(c(t) - c_0)];$$

where $q_0$ is the conversion factor q(c) at a particular, known x-ray tube current value (e.g., $q_0 = 8.5$), s is a scaling parameter (e.g., $s = 1.0 \times 10^{-5}$), and $c_0$ is a tube input reference value (e.g., $c_0 = 9915$). Alternatively s can be made a function of $c_0$. It should be noted that the conversion factor q also changes with the DAS sampling rate. (This simple linear relationship will not be discussed here.) Note that here the tube input value is in some measurement unit and not the x-ray tube current milli-amp. The measurement unit can be converted to the x-ray tube current in mA by a simple scaling.

Next, at step 304, the average measured flux, or average reference channel reading, for both the left side and the right side is calculated. The average left reference channel reading, $R_l(t)$, may be expressed as:

$$R_l(t) = \frac{1}{m} \sum_{i=1}^{m} p(i, t);$$

where, p(i,t) is the detector reading for cell i and view t, and m is the parameter that controls the number of channels to average. In an exemplary embodiment of the present invention, there are three reference channels (m=3). Note that in these equations, the detector row notation is dropped for simplicity. It is understood that this operation needs to be repeated for each row in the detector.

At this point, the predicted value could be compared against the measured value for reference blockage. However, exemplary embodiments of the present invention perform additional steps to verify the data and to avoid cases where the reference channels are slightly blocked and non-optimal reference values are used for normalization. Although there is only one set of reference channels, or reference detectors 44, located on the left side of the detector, the rightmost detector channels are utilized as temporary reference channels. This is based on the observation that unless the scanned object is very large, the left channel blockage is likely caused by the off-centered positioning of the patient. Therefore, there is a good probability that the right side channels are not blocked.

The right reference reading, $R_r(t)$, may be represented as:

$$R_r(t) = \frac{1}{n} \sum_{i=N-n+1}^{N} p(i, t);$$

where n is a parameter that controls the number of channels to average (e.g., n=3), and N is the total number of detector channels in a row. Since the detector gains for the left reference channels and the right-most channels are likely to be different, $R_r(t)$ is scaled by a scaling factor. This scaling, or gain, factor is determined by the ratio of the left and right channel readings during air scan (no object in the beam path). For simplicity, $R_r(t)$ is utilized to denote the properly scaled average reading of the right-most channel.

At step 306, the predicted flux values ($f_r(t)$ and $f_l(t)$) are checked and corrected for errors in one or more of the conversion factors. In general, the predicted values based on the x-ray tube current, $f_l(t)$ and $f_r(t)$, are used as the bases of reference correction. However, to guard against the situation in which either the conversion factor, gain and/or the current value are wrong, it is necessary to make sure that the magnitude of these values is at least a significant fraction of the measured x-ray flux ($R_l(t)$ and $R_r(t)$) at the reference channels. To accomplish this, the following operation is performed:

$$f_l(t) = \begin{cases} f_l(t), & f_l(t) \geq \alpha R_l(t) \\ \varepsilon R_l(t), & f_l(t) < \alpha R_l(t) \end{cases}, \text{ and } f_r(t) = \begin{cases} f_r(t), & f_r(t) \geq \alpha R_r(t) \\ \varepsilon R_r(t), & f_r(t) < \alpha R_r(t) \end{cases}.$$

In an exemplary embodiment of the present invention, the parameter $\alpha$, is set to 0.95 and the scaling parameter $\varepsilon$, is set to 0.97. It should be noted that $f_l(t)$ and $R_l(t)$ would be equal under non-blocked conditions.

At step 308, the least blocked side is selected to be utilized as the reference correction value. The ratio of the measured reference signal against the predicted reference signal is calculated for both the left side and the right side to ensure that the side with the highest ratio is always used for reference correction. This is to ensure that if one of the two sides is blocked by the patient (even if it is only slightly), the unblocked side is used. The ratios, $\eta_l(t)$ and $\eta_r(t)$, are calculated as follows:

$$\eta_l(t) = \frac{R_l(t)}{f_l(t)}, \text{ and } \eta_r(t) = \frac{R_r(t)}{f_r(t)}$$

$\eta_l(t)$ is compared against $\eta_r(t)$ and the side with a higher ratio is used for the reference correction. For illustration, assume that $\eta_r(t) > \eta_l(t)$. (The other case can be treated in exactly the same manner by substituting the subscript "r" by "l" in all the following equations.)

At step 310, the reference correction value for the previous view scaled by the x-ray tube current change is utilized if both sides are blocked. This determination of the reference correction value, $w(t)$, can be expressed as the equation:

$$w(t) = \begin{cases} R_r(t), & \eta_r(t) \geq \delta \\ \frac{w(t-1)c(t)}{c(t-1)}, & \eta_r(t) < \delta \end{cases};$$

where $\delta$ is a parameter (e.g., $\delta=0.95$ in an exemplary embodiment of the present invention). This equation indicates that the measured reference value should be utilized only if it is more than 95% of the predicted signal based on the x-ray tube current. If this condition does not hold, it indicates that channels, or detectors, on both sides of the detector array 6 are blocked (since the higher of the two sides does not meet the requirement) and that the measured reference value is not reliable. In the case where both sides are blocked, the reference correction value of the previous view, $w(t-1)$, scaled by the x-ray tube current change $c(t)/c(t-1)$ is used as the reference correction value $w(t)$. For the final reference correction, the measured projection is divided by the correction value, $w(t)$.

In an exemplary embodiment of the present invention, the processing described above in reference to FIG. 3 may be implemented by computer instructions located on the processing device 32 with data being stored on the data storage device 30. In an alternate exemplary embodiment, the processing described in FIG. 3 may be implemented by a processor located remotely from the processing device 32.

The formulas described in reference to FIG. 3 are utilized by an exemplary embodiment of the present invention. As is known in the art, other formulas may be utilized to perform the steps described in reference to FIG. 3. For example, in the $w(t)$ calculation, only one preceding view $w(t-1)$ is used when both sides are blocked. To improve robustness of the algorithm, multiple preceding views can be used. In the example listed above, only the left reference channel is designed into the detector. However, one can design a set of right reference channels to the right of the detector to improve the performance, since the further away a channel is from the center, the less is the probability that the channel will be blocked.

In accordance with an exemplary embodiment of the present invention, while a method and system for reference normalization for blocked reference channels in an x-ray image, generated by an imaging system is described and discussed herein with reference to a computed tomography (CT) imaging system, it should be understood that the method and system of the invention may be applied to other imaging systems (e.g., Magnetic Resonance Imaging (MRI).

The ability to perform reference normalization for blocked reference channels when the x-ray tube current has the potential of changing from view to view can lead to more accurate images being produced by the imaging system. In addition, the ability to use regular channels, or detectors, that are located on the radiation detector array to supplement the reference channels may lead to less lost data due to reference channel blockage. Further, the ability to utilize a previous reference correction value when channels at both sides of the radiation detector array are blocked may also lead to improved performance.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. The technical effect of the executable instructions is to enhance the quality of the x-ray image when one or more of the reference channels are blocked, resulting in less radiation exposure by decreasing the number of images taken. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for performing reference normalization for a measured projection created by an imaging system that includes a radiation detector array with a right and left edge, the method comprising:
receiving a projection dataset created by the imaging system in response to a varying x-ray tube current, the projection dataset including a view;
calculating predicted fluxes for right and left sets of reference channels within the view, wherein the right set of reference channels is located proximate at the right edge of the detector array and the left set of reference channels is located proximate to the left edge of the detector array;
calculating average actual fluxes for the right and left sets of reference channels;
determining a reference correction value for the view based on the predicted reference fluxes and the average actual fluxes;
substituting a previous reference correction value scaled by an x-ray tube current change for the reference correction value if the right and left sets of reference channels are blocked; and
applying the reference correction value to the view.

2. The method of claim 1 wherein the imaging system is a computed tomography imaging system.

3. The method of claim 1 wherein the imaging system is a wide-bore computed tomography imaging system.

4. The method of claim 1 wherein the right set of reference channels is implemented by detector cells in the detector array.

5. The method of claim 1 wherein the left set of reference channels is implemented by reference detector cells in the detector array.

6. The method of claim 1 wherein there are three reference channels in each set.

7. The method of claim 1 wherein:
the projection dataset further includes a measured x-ray tube current and a conversion factor for each set of reference channels;
the predicted flux for the right set of reference channels is calculated by multiplying the measured x-ray tube current and the conversion factor for the right set of reference channels; and
the predicted flux for the left set of reference channels is calculated by multiplying the measured x-ray tube current and the conversion factor for the left set of reference channels.

8. The method of claim 1 wherein:
the projection dataset further includes a reference channel reading for each reference channel;
the average actual flux for the right set of reference channels is calculated by taking an average of the reference channel readings for the reference channels in the right set; and
the average actual flux for the left set of reference channels is calculated by taking an average of the reference channel readings for the reference channels in the left set.

9. The method of claim 1 wherein the determining a reference correction value includes:
correcting the predicted fluxes for errors in conversion factors; and
setting the reference correction value for the view to the average actual flux from the set of reference channels with the highest ratio of the average actual flux to the predicted flux.

10. The method of claim 1 wherein the the right and left sets of reference channels are blocked if the ratio of the average actual flux to the predicted flux is less than a selected parameter.

11. The method of claim 1 wherein applying the reference correction value to the view includes dividing the measured projection by the reference correction value.

12. A method for performing reference normalization for a projection created by an imaging system that includes a radiation detector array with a right and left edge, the method comprising:
operating the imaging system so as to create a projection dataset responsive to an object, wherein the imaging system is operated at varying x-ray tube currents to create the projection dataset and the projection dataset includes a view;
calculating predicted fluxes for right and left sets of reference channels within the view, wherein the right set of reference channels is located proximate at the right edge of the detector array and the left set of reference channels is located proximate to the left edge of the detector array;
calculating average actual fluxes for the right and left sets of reference channels;
determining a reference correction value for the view based on the predicted reference fluxes and the average actual fluxes;
substituting a previous reference correction value scaled by an x-ray tube current change for the reference correction value if the right and left sets of reference channels are blocked; and
applying the reference correction value to the view.

13. The method of claim 12 wherein the object is a patient.

14. The method of claim 12 wherein the imaging system is a computed tomography imaging system.

15. The method of claim 12 wherein the right set of reference channels contains detector cells in the detector array.

16. The method of claim 12 wherein:
the projection dataset further includes a measured x-ray tube current and a conversion factor for each set of reference channels;
the predicted flux for the right set of reference channels is calculated by multiplying the measured x-ray tube current and the conversion factor for the right set of reference channels; and
the predicted flux for the left set of reference channels is calculated by multiplying the measured x-ray tube current and the conversion factor for the left set of reference channels.

17. The method of claim 12 wherein:
the projection dataset further includes a reference channel reading for each reference channel;

the average actual flux for the right set of reference channels is calculated by taking an average of the reference channel readings for the reference channels in the right set; and the average actual flux for the left set of reference channels is calculated by taking an average of the reference channel readings for the reference channels in the left set.

18. The method of claim 12 wherein the determining a reference correction value includes:
  correcting the predicted fluxes for errors in conversion factors; and
  setting the reference correction value for the view to the average actual flux from the set of reference channels with the highest ratio of the average actual flux to the predicted flux.

19. A medium encoded with a machine-readable computer program code for performing reference normalization for a projection created by an imaging system that includes a radiation detector array with a right and left edge, the medium including instructions to implement a method comprising:
  receiving a projection dataset created by the imaging system in response to a varying x-ray tube current, the projection dataset including a view;
  calculating predicted fluxes for right and left sets of reference channels within the view, wherein the right set of reference channels is located proximate at the right edge of the detector array and the left set of reference channels is located proximate to the left edge of the detector array;
  calculating average actual fluxes for the right and left sets of reference channels;
  determining a reference correction value for the view based on the predicted reference fluxes and the average actual fluxes;
  substituting a previous reference correction value scaled by an x-ray tube current change for the reference correction value if the right and left sets of reference channels are blocked; and
  applying the reference correction value to the view.

20. A system for performing reference normalization for a projection, the system comprising:
  a gantry having an x-ray source and a radiation detector array, wherein said gantry defines an object cavity, said x-ray source and said radiation detector array are rotatingly associated with said gantry so as to be separated by said object cavity and said detector array includes a right and left edge;
  an object support structure movingly associated with said gantry so as to allow communication with said object cavity; and
  a processing device including instructions to implement the method comprising:
    receiving a projection dataset created by the imaging system in response to a varying x-ray tube current, the projection dataset including a view;
    calculating predicted fluxes for right and left sets of reference channels within the view, wherein the right set of reference channels is located proximate at the right edge of the detector array and the left set of reference channels is located proximate to the left edge of the detector array;
    calculating average actual fluxes for the right and left sets of reference channels;
    determining a reference correction value for the view based on the predicted reference fluxes and the average actual fluxes;
    substituting a previous reference correction value scaled by an x-ray tube current change for the reference correction value if the right and left sets of reference channels are blocked; and
    applying the reference correction value to the view.

21. A system for performing reference normalization for a projection, the system comprising:
  an imaging system including a radiation detector array with a right and left edge;
  an object disposed so as to be communicated with the imaging system, wherein the imaging system generates a projection dataset responsive to the object and to a varying x-ray tube current, the projection dataset including a view; and
  a processing device, wherein the processing device:
    receives the projection dataset created by the imaging system;
    calculates predicted fluxes for right and left sets of reference channels within the view, wherein the right set of reference channels is located proximate at the right edge of the detector array and the left set of reference channels is located proximate to the left edge of the detector array;
    calculates average actual fluxes for the right and left sets of reference channels;
    determines a reference correction value for the view based on the predicted reference fluxes and the average actual fluxes;
    substitutes a previous reference correction value scaled by an x-ray tube current change for the reference correction value if the right and left sets of reference channels are blocked; and
    applies the reference correction value to the view.

22. The system of claim 21, wherein the object is a patient.

23. The system of claim 21, wherein the imaging system is a computed tomography imaging system.

24. The system of claim 21 wherein the imaging system a wide-bore scanner.

* * * * *